(12) United States Patent
Ferris, Jr.

(10) Patent No.: US 7,799,793 B2
(45) Date of Patent: Sep. 21, 2010

(54) N-ALKYLATED RIFAMPIN

(75) Inventor: William V. Ferris, Jr., Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 277 days.

(21) Appl. No.: 12/109,489

(22) Filed: Apr. 25, 2008

(65) Prior Publication Data
US 2008/0268010 A1 Oct. 30, 2008

Related U.S. Application Data

(60) Provisional application No. 60/914,346, filed on Apr. 27, 2007.

(51) Int. Cl.
C07D 413/04 (2006.01)
A61K 31/497 (2006.01)
A61P 31/04 (2006.01)

(52) U.S. Cl. .................. 514/254.11; 540/458
(58) Field of Classification Search ................. 540/458; 514/254.11
See application file for complete search history.

(56) References Cited

U.S. PATENT DOCUMENTS

| 4,600,518 A | 7/1986 | Ries |
| 4,675,180 A | 6/1987 | Günter |

*Primary Examiner*—Bruck Kifle
(74) *Attorney, Agent, or Firm*—Scott A. Marks; Campbell Nelson Whipps LLC

(57) ABSTRACT

Compounds of the formula:

where X and Y are each independently H, halo, or $C_1$-$C_6$ straight or branched chain substituted or unsubstituted alkyl.

9 Claims, No Drawings

N-ALKYLATED RIFAMPIN

RELATED APPLICATIONS

This application claims the benefit of Provisional Application No. 60/914,346, filed on Apr. 27, 2007, which application is hereby incorporated herein by reference in its entirety.

FIELD

This application relates to rifampin derivatives, more particularly to N-alkylated rifampin derivatives and anti-infective compositions and articles containing such derivatives.

BACKGROUND

Rifampin, also known as rifampicin, is a semisynthetic macrocyclic bactericidal antibiotic derived from *Amycolatopsis mediterranei*. Rifampin inhibits DNA-dependent RNA polymerase activity through interaction with bacterial RNA polymerase. Rifampin is used in the treatment of mycobacterium infections and may be used in combination with fusidic acid in the treatment of methicillin-resistant *Staphylococcus aureus* (MRSA). In addition, rifampin, in combination with other drugs, is used to treat infection by *Listeria* species, *Haemophilus influenzae, Neisseria gonorrhoeae*, and *Legionella pneumophila*.

Further, rifampin, in combination with minocycline, has been incorporated into polymeric implantable medical devices, such as catheters, to reduce the risk of infection associated with implantation of the devices. Many of these rifampin-containing implantable medical devices are sterilized via treatment with ethylene oxide (EtO).

BRIEF SUMMARY

A major N-alkylated degradant has been detected following ethylene oxide sterilization of polymeric material incorporating rifampin. The N-alkylated rifampin compound has been synthesized and characterized. The N-alkylated rifampin compound has activity against *Staphlococcus aureus*.

In various embodiments the invention provides an isolated compound of the formula:

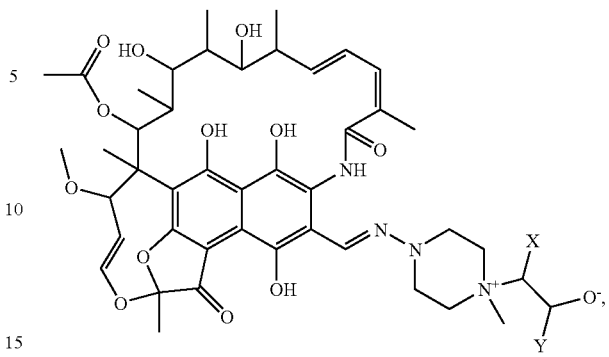

where X and Y are each independently H, halo, or $C_1$-$C_6$ straight or branched chain substituted or unsubstituted alkyl, with the proviso that X and Y are not both H.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein, an "effective amount" of an anti-infective agent is an amount that prevents, reduces the severity of, or delays an infection.

In the context of the present disclosure, the terms "treat", and the like, as it refers to a disease, means alleviate, slow the progression, prevent, attenuate, or cure the disease.

As used herein, "rifampin" refers to 5,6,9,17,19,21-Hexahydroxy-23-methoxy-2,4,12,16,18,20,22-heptamethyl-8-[N-(4-methyl-1-piperazinyl)formimidoyl]-2,7-(epoxypentadeca[1,11,13]trienimino)-naphtho[2,1-b]furan-1, 11(2H)-dione 21-acetate and pharmaceutically acceptable salts, solvates, hydrates, isomers, and polymorphs thereof. Rifampin is a compound having the following structure:

(I)

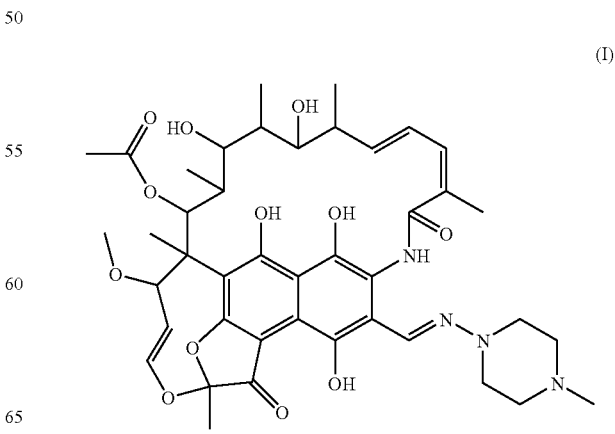

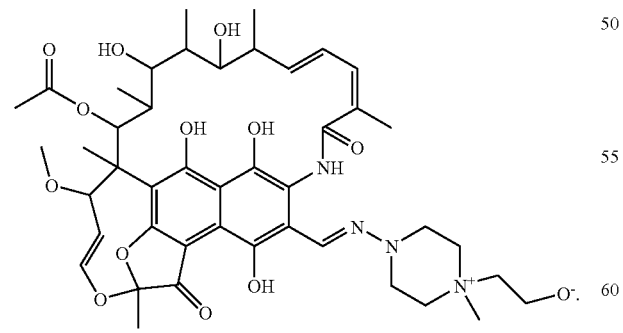

Pharmaceutical compositions containing the compound are also provided.

In various embodiments the invention provides a compound of the formula:

Reference herein to any chemical structure or compound should be construed as reference to the compound or structure and any pharmaceutically acceptable salts, solvates, hydrates, isomers, and polymorphs thereof.

In the context of the present disclosure, "isolated" as it relates to N-alkylated rifampin compounds means the N-alkylated rifampin compound is in an environment other than a polymeric material. For example, an isolated n-alkylated rifampin derivative may be in a pharmaceutical composition such as a pill, tablet, injectable solution or the like or in a dried powder form, etc.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure describes, inter alia, N-alkylated rifampin derivatives, compositions and articles including such derivatives, and methods of using the derivatives in the treatment of infection.

Compounds

In various embodiments, the invention provides an isolated N-alkylated rifampin compound having the following structure:

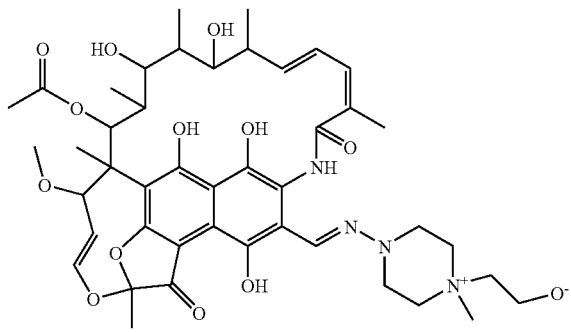

(II)

The compound of Formula II may be synthesized by reacting rifampin with EtO as follows:

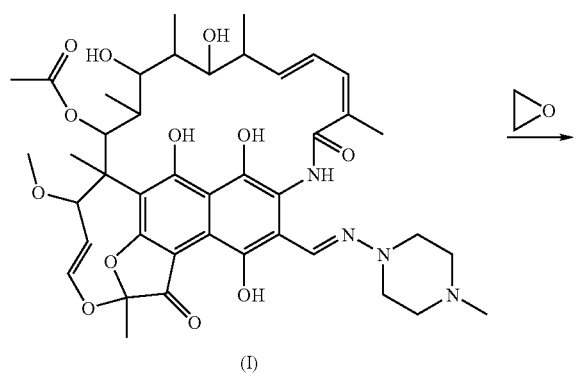

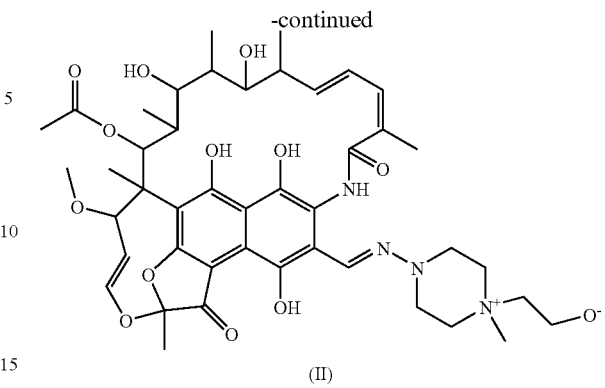

(II)

In various embodiments, the invention provides N-alkylated rifampin compounds having the following structure:

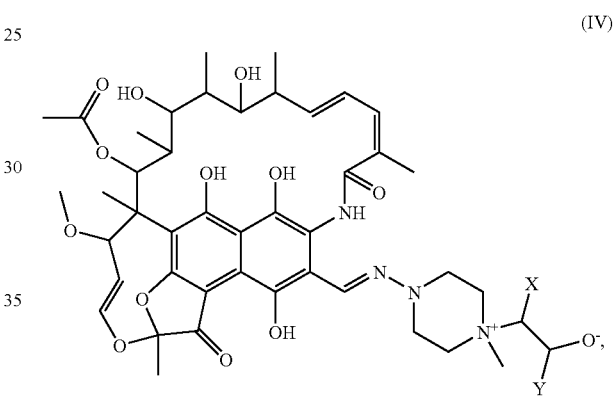

(IV)

where X and Y are each independently H, halo, or $C_1$-$C_6$ straight or branched chain substituted or unsubstituted alkyl, with the proviso that X and Y are not both H.

In various embodiments, X and Y are each independently H or $C_1$-$C_3$ straight or branched chain unsubstituted alkyl.

Compounds of Formula IV may be synthesized by reacting rifampin with an ETO derivative (a compound of Formula III) as follows:

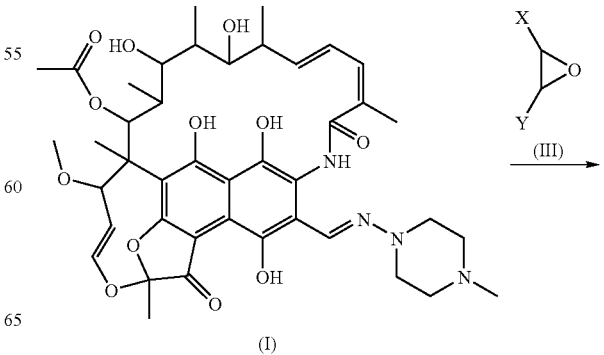

(I)

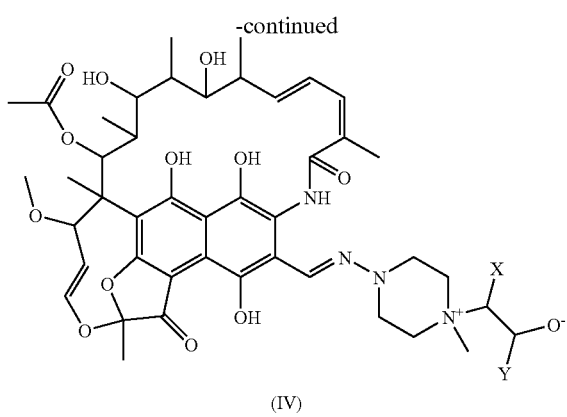

(IV)

Pharmaceutical Formulations

In various embodiments, the invention provides pharmaceutical formulations including a compound of Formula II or IV and a pharmaceutically acceptable vehicle, such as an inert diluent or an assimilable edible carrier. The compounds may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any, unit dosage form should be pharmaceutically acceptable and substantially non-toxic in the amounts employed. In addition, the active compound may be incorporated into sustained-release preparations and devices.

Compositions including a compound of Formula II or IV may also be administered intravenously or intraperitoneally by infusion or injection. Solutions may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active composition in the required amount in the appropriate solvent with various of the other ingredients enumerated above, as required, followed by filter sterilization, EtO sterilization, or sterilization by radiation. In the case of sterile powders for the preparation of sterile injectable solutions, the methods of preparation may include vacuum drying and freeze drying techniques, which yield a powder of the active ingredient plus any additional desired ingredient present in the previously sterilized solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compositions of the invention in a liquid composition, such as a lotion, will be about 0.1-50 wt-%, (e.g., about 0.5-5 wt %). The concentration in a semi-solid or solid composition such as a gel or a powder will be about 0.1-5 wt-% (e.g., about 0.5-2.5 wt-%).

The amount of the composition required for use in treatment will vary not only with the particular salt selected but also with the route of administration, the nature of the condition being treated, and the age and condition of the patient, and will ultimately be at the discretion of the attendant physician or clinician.

In general, however, a suitable dose will be in the range of from about 0.1 to about 150 mg/kg, e.g., from about 10 to about 75 mg/kg of body weight per day, such as 3 to about 50 mg per kilogram body weight of the recipient per day.

The compositions are conveniently administered in unit dosage form; for example, containing 5 to 1000 mg, conveniently 10 to 750 mg or 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Following i.m. administration, the compositions of the invention enter the blood stream within about 10-15 minutes and reach a maximum concentration in the blood within one hour of administration, at which point they can be found throughout the circulatory related organs.

Polymeric Materials

In various embodiments, the invention provides a polymeric material having a compound of Formula IV associated with the polymeric material. The polymeric material may be any suitable shape and may take any suitable form. For example, the polymeric material may be in the form of a tube, sheath, sleeve, boot, disc, or the like. The polymeric material may be extruded, molded, or otherwise formed. Examples of commonly used suitable polymeric materials include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE).

The polymeric material may be biodegradable, such as synthetic or natural bioabsorbable polymers. Synthetic bioabsorbable polymeric materials that can be used to form the coating layers include poly(L-lactic acid), polycaprolactone, poly(lactide-co-glycolide), poly(ethylene-vinyl acetate), poly(hydroxybutyrate-covalerate), polydioxanone, poly-orthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly (iminocarbonate), copoly(ether-esters) such as PEO/PLA, polyalkylene oxalates, polyphosphazenes, and polyarylates including tyrosine-derived polyarylates. According to another exemplary embodiment, the polymeric materials can be natural bioabsorbable polymers such as, but not limited to, fibrin, fibrinogen, cellulose, starch, collagen, and hyaluronic acid. "Biodegradable", "bioerodable", and "bioabsorbable" are used herein interchangeably.

The polymeric material may be in the form of a boot designed to be placed around an implantable medical device or a disc, for example as described in U.S. Provisional Patent Application Ser. No. 60/912,234, entitled "REDUCTION OF INFECTION ASSOCIATED WITH MEDICAL DEVICE", filed on Apr. 17, 2007, and which application is hereby incorporated herein by reference in its entirety to the extent that it does not conflict with the disclosure presented herein. The polymeric material with associated compound according to Formula II or IV may be placed in a subcutaneous pocket or may be placed on or about an implantable medical device. In various embodiments, the polymeric material is bonded, adhered to, coated on, or otherwise attached to the implantable medical device.

A compound according to Formula II or IV may be present in the polymeric material at any suitable concentration. For example, a compound according to Formula II or may comprise 0.1% to 50%, 0.1% to 20%, 0.1% to 5%, 1% to 10%, etc. of the weight of the article. A compound according to Formula II or IV may be incorporated into the polymeric material in a variety of ways. For example, a compound according to Formula II or IV can be covalently grafted to the polymeric material, either alone or with a surface graft polymer. Alternatively, a compound according to Formula II or IV may be coated onto the surface of the polymeric material either alone or intermixed with an overcoating polymer. A compound according to Formula II or IV may be physically blended with the polymeric material as in a solid-solid solution. A compound according to Formula II or IV may be impregnated into the polymeric material by swelling the polymer in a solution of the appropriate solvent. Any means of incorporating a compound according to Formula II or IV into or on a polymeric material may be used. Regardless of how the compounds according to Formula II or IV are associated with the polymeric material, it is desirable that the compounds according to Formula II or IV are incorporated in an amount effective to prevent, reduce the severity, or delay an infection.

Methods

In various embodiments, the invention provides a method for inhibiting growth of bacteria, such as *S. aureus*, by contacting the bacteria with a compound of Formula II or IV.

In various embodiments, the invention provides a method for treating an infection in a patient, such as *S. aureus*, by administering to the patient an effective amount of a compound of Formula II or IV.

In various embodiments, the invention provides a method for preventing an infection in a patient, such as *S. aureus*, by administering to the patient an effective amount of a compound of Formula II or IV.

EXAMPLE

As described in U.S. patent application Ser. No. 11/535,762, entitled "STERILIZED MINOCYCLINE AND RIFAMPIN-CONTAINING MEDICAL DEVICE", filed on Sep. 27, 2006 and having it has been found that ethylene oxide (EtO) sterilization of rifampin containing polymeric articles results in substantial degradation of rifampin, which patent application is hereby incorporated herein by reference in its entirety to the extent that it does not conflict with the present disclosure. Twenty-eight to 49% of the degradant has been observed after one cycle of EtO sterilization, with only 5% of rifampin being recoverable after five EtO sterilization cycles. The disclosure that follows describes the characterization and synthesis of the EtO sterilized rifampin degradant.

Rifampin was reacted with ethylene oxide as described in Scheme 1. Briefly, rifampin was reacted with ethylene oxide in methanol at 50-55° C. to produce the N-alkylated rifampin compound according to Formula (II).

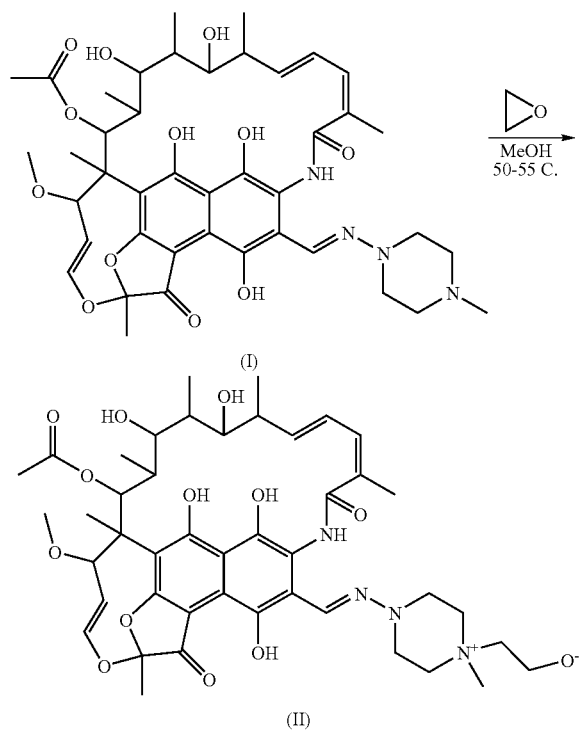

Scheme 1: Reaction of Rifampin with Ethylene Oxide

A series of synthesis and purification reactions were performed according to Scheme 1. Table 1 describes the conditions and results of some of these reactions.

TABLE 1

Results from reactions according to Scheme 1

| Reaction | Rifampin (g) | Ethylene Oxide (g) | Time (h) | MeOH (ml) | Yield | Purity |
|---|---|---|---|---|---|---|
| 1 | 1.07 | 9.8 | 8.0 | 40 | 81% | 88.1% |
| 2 | 5.00 | 15.9 | 9.0 | 50 | 72% | 98.6% |
| 3 | 5.01 | 29.0 | 19.5 | 40 | 80% | 98.5% |
| 4 | 5.01 | 11.0 | 17.5 | 30 | 82% | 98.4% |
| 5 | 15.08 | 20.7 | 16.5 | 90 | 87% | 98.3% |

Reactions 1 and 3-5 were at 50° C., and reaction 2 was performed at 55° C. Following each reaction, the resultant solution was purged with argon to remove residual ethylene oxide (ETO). For reaction 1, the resultant methanolic mixture was added over 10 minutes to a solution of 1:2 methyl tert-butyl ether (MTBE)/heptane (135 ml) at ambient temperature. The resulting slurry was cooled to 0-5° C. over 30 minutes, stirred for one hour, filtered (washed with 30 ml cold 1:2 MTBE/heptane), and dried under vacuum to afford 908 mg of the compound of Formula II.

In reactions 2-5, the argon purge evaporated most of the solvent, causing the residue to precipitate. It was found that the residue could be recrystallized from the same volume of methanol in the same pot, resulting in improved purity.

A more detailed discussion of reaction 5, which is a representative reaction, follows. EtO (20.7 g, 470 mmol, Aldrich) was bubbled through a slurry of rifampin (15.1 g, 18.3 mmol, Spectrum Chemical Mfr. Corp) in methanol (90 ml, Pharmco USP/NF grade) at 50° C. for 50 min. The mixture became homogeneous upon stirring for several hours. The mixture was analyzed by HPLC after 16.5 hours and determined to contain 90.4% (AUC) of a compound according to Formula II and 5.4% (AUC) rifampin. The mixture was heated to reflux with an argon purge until the solvent had nearly completely evaporated. Methanol (90 ml) was added at 60 C and stirred until the mixture became homogeneous. The mixture was cooled to ambient temperature over 2 hours. At 28° C., some seed crystals were added. At this time, a precipitate formed. The resulting slurry was cooled to 0-5° C. over 30 minutes, stirred for 1 hour, and filtered (washed with 15 ml and 5 ml cold methanol). The collected solid was dried at ambient temperature under vacuum for 1 hour to afford the compound of Formula II (13.8 g, 87%) as an orange solid at 98.3% (AUC) purity. The solid was dried under vacuum at ambient temperature for an additional 7 days to afford a compound according to Formula II as an orange solid at 98.1% (AUC) purity. $^1$H NMR and mass spectra (not shown) were consistent with the assigned structure.

HPLC procedures for determining the purity of the compound of Formula II in reaction 5 were as follows:

| Time (min) | Flow (ml/min) | % A | % B |
|---|---|---|---|
| 0 | 1.0 | 88 | 12 |
| 10 | 1.0 | 64 | 36 |
| 25 | 1.0 | 25 | 75 |

Column: Phenomenex Prodigy ODS(2) C18, 4.6 × 150 mm, 5 micrometers
A = Acetonitrile
B = 1.4 g/l pH = 6.8 phosphate buffer in water Stability testing (not shown) revealed that degradation over time, particularly at higher temperatures, resulted. Accordingly, it may be desirable to store the material at about −20° C. prior to use.

The ability of the compound of Formula II to inhibit growth of *Staphylococcus aureus* (ATCC 29213) was determined in vitro. Briefly, agar plates were coated with *S. aureus* and discs containing 5 μg of rifampin and 5 μg of a compound of Formula II were placed on the coated plates. The plates were incubated at 35° C. for 24 hours and the zones of inhibition of the rifampin and the compound of Formula II were determined. The zone of inhibition for the rifampin loaded disc was 28 mm. The zone of inhibition for the disc with a compound of Formula II was 18 mm. Minimum Inhibitory Con centrations (MICs) were also evaluated for both Rifampin and the compound of Formula II: Baseline MIC for Rifampin is between 3.13 ng/ml and 6.25 ng/ml, Baseline MIC for the compound of Formula II is between 2 μg/ml and 4 μg/ml.

Thus, embodiments of the N-ALKYLATED RIFAMPIN are disclosed. One skilled in the art will appreciate that the present invention can be practiced with embodiments other than those disclosed. The disclosed embodiments are presented for purposes of illustration and not limitation.

What is claimed is:

1. A compound of the formula:

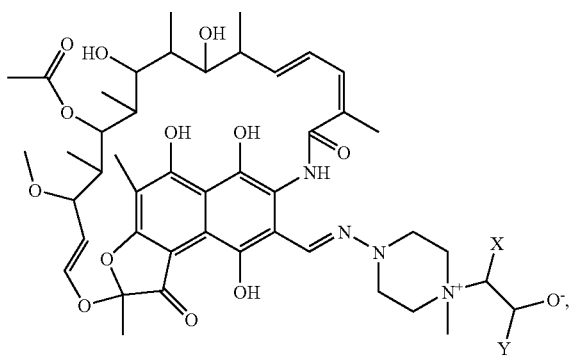

or a pharmaceutically acceptable salt or isomer thereof,
wherein X and Y are each independently H, halo, or $C_1$-$C_6$ straight or branched chain unsubstituted alkyl, with the proviso that X and Y are not both H.

2. A compound according to claim 1, wherein wherein X and Y are each independently H or $C_1$-$C_3$ straight or branched chain unsubstituted alkyl.

3. A pharmaceutical composition comprising:
a compound according to claim 1; and
a pharmaceutically acceptable carrier.

4. A method of inhibiting growth of bacteria, comprising:
contacting the bacteria with a compound according to claim 1.

5. A method for treating a bacterial infection in a patient, comprising:
administering to the patient an effective amount of a compound according to claim 1.

6. An isolated compound of the formula:

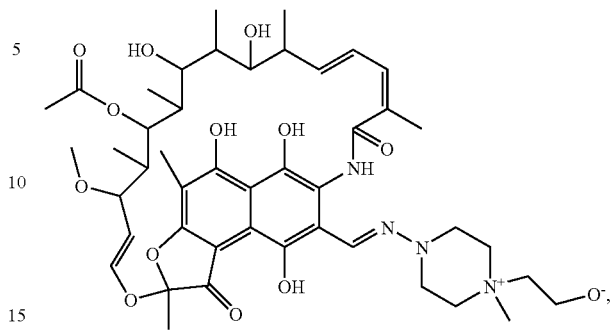

or a pharmaceutically acceptable salt or isomer thereof.

7. A pharmaceutical composition comprising:
a compound of the formula:

(II)

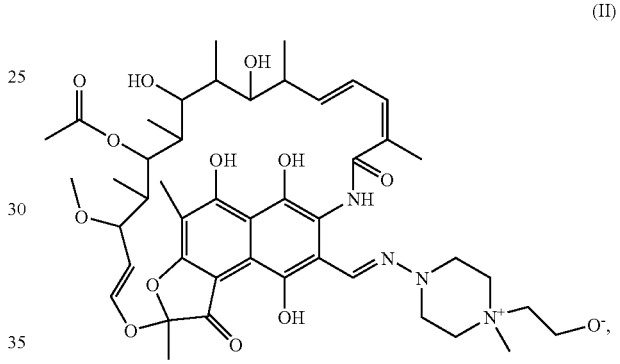

or a pharmaceutically salt or isomer thereof; and
a pharmaceutically acceptable vehicle.

8. A method for treating a bacterial infection in a patient, comprising:
administering to the patient a composition according to claim 7, wherein the composition comprises an effective amount of the compound of Formula II.

9. A method for preventing a bacterial infection in a patient, comprising:
administering to the patient a composition according to claim 7, wherein the composition comprises an effective amount of the compound of Formula II.

* * * * *